US012751711B2

(12) United States Patent
Dooney, Jr. et al.

(10) Patent No.: US 12,751,711 B2
(45) Date of Patent: Oct. 6, 2026

(54) VARIABLE DENSITY SOFT ANCHORS AND METHODS OF TISSUE REPAIRS

(71) Applicant: ARTHREX, INC., Naples, FL (US)

(72) Inventors: Thomas Dooney, Jr., Naples, FL (US); Nirav Patel, Naples, FL (US); Michael Schmidt, Naples, FL (US); Shaun G. Leblanc, Naples, FL (US); Matthew Herrington, Naples, FL (US)

(73) Assignee: ARTHREX, INC., Naples, FL (US)

( * ) Notice: Subject to any disclaimer, the term of this patent is extended or adjusted under 35 U.S.C. 154(b) by 439 days.

(21) Appl. No.: 18/366,077

(22) Filed: Aug. 7, 2023

(65) Prior Publication Data

US 2025/0049429 A1 Feb. 13, 2025

(51) Int. Cl.
*A61B 17/04* (2006.01)
*A61B 17/06* (2006.01)

(52) U.S. Cl.
CPC .. *A61B 17/0401* (2013.01); *A61B 2017/0459* (2013.01); *A61B 2017/06185* (2013.01)

(58) Field of Classification Search
CPC .......... A61B 17/0401; A61B 17/06166; A61B 2017/0459; A61B 2017/0464; A61B 2017/06185; A61B 2017/0406; A61B 2017/0414; A61B 2017/0445; A61B 2017/042
See application file for complete search history.

(56) References Cited

U.S. PATENT DOCUMENTS

| | | | | |
|---|---|---|---|---|
| 7,905,903 B2 * | 3/2011 | Stone | A61B 17/0401 606/232 |
| 8,361,113 B2 * | 1/2013 | Stone | A61F 2/0811 606/232 |
| 8,409,253 B2 * | 4/2013 | Stone | A61B 17/0469 606/232 |
| 9,237,888 B2 | 1/2016 | Sengun et al. | |
| 2008/0281355 A1 * | 11/2008 | Mayer | B29C 61/0608 606/228 |
| 2011/0213385 A1 | 9/2011 | Ewers et al. | |
| 2011/0264141 A1 * | 10/2011 | Denham | A61B 17/0401 606/232 |
| 2011/0276137 A1 * | 11/2011 | Seedhom | A61F 2/08 623/13.11 |
| 2012/0253389 A1 | 10/2012 | Sengun et al. | |
| 2014/0052178 A1 | 2/2014 | Dooney, Jr. | |
| 2014/0316460 A1 * | 10/2014 | Graul | A61B 17/0401 606/228 |

(Continued)

OTHER PUBLICATIONS

International Search Report and Written Opinion for International Application No. PCT/US2024/037998 dated Nov. 6, 2024.

*Primary Examiner* — Dianne Dornbusch
(74) *Attorney, Agent, or Firm* — Potomac Law Group, PLLC

(57) ABSTRACT

Surgical anchor constructs, fixation devices, and methods of manufacturing, as well as methods for tissue repairs are disclosed. A soft suture anchor has a sheath with varying densities along the length of the sheath. The anchor sheath can have different segments with different densities which can be provided in a pattern or a random manner. The segments with different densities allow secure fixation of the soft anchor within bone, and attachment of first tissue to second tissue.

14 Claims, 3 Drawing Sheets

(56) References Cited

U.S. PATENT DOCUMENTS

| | | | | |
|---|---|---|---|---|
| 2015/0032157 | A1 | 1/2015 | Dooney, Jr. et al. | |
| 2015/0066081 | A1* | 3/2015 | Martin | D04B 21/202 606/228 |
| 2016/0074030 | A1 | 3/2016 | Dreyfuss et al. | |
| 2017/0296182 | A1* | 10/2017 | Allen | D04C 3/48 |
| 2019/0380708 | A1* | 12/2019 | Allen | D04C 3/30 |
| 2020/0360009 | A1* | 11/2020 | Lombardo | A61B 17/0401 |
| 2020/0375744 | A1* | 12/2020 | Sheth | A61F 2/30767 |
| 2021/0068807 | A1* | 3/2021 | Miller | A61B 17/0401 |
| 2022/0257233 | A1 | 8/2022 | Haarer | |

* cited by examiner

VARIABLE DENSITY SOFT ANCHORS AND METHODS OF TISSUE REPAIRS

BACKGROUND

The disclosure relates to the field of surgery and, more specifically, to surgical suture constructs and methods of making, and tissue repairs for reconstructive surgeries.

SUMMARY

Surgical flexible constructs, fixation devices, methods of making, and methods of tissue repairs are disclosed.

A surgical construct can include a soft anchor sheath having varying densities along its length. A soft anchor sheath can have a non-regular braid, weave, or knit density pattern, or combinations thereof. A soft anchor sheath can be manufactured with varying and controlled sheath density based on a particular application. A surgical construct can create a knotless, self-tensioning, self-locking, reinforced repair. A surgical construct can be employed in knotless or knotted fixation of first tissue to second tissue, for example, fixation of soft tissue to bone.

Methods of tissue repairs are also disclosed. A knotless surgical construct can provide tissue to tissue fixation without any knot formation, with fewer passing steps, and with increased fixation and soft tissue compression. A soft anchor sheath having varying densities allows for better bunching or setting of the anchor in bone. A soft anchor sheath having varying densities can allow for the anchor to set more reproducibly.

DETAILED DESCRIPTION

The disclosure provides surgical fixation devices, constructs, methods for manufacturing, and tissue repairs and reconstructions.

A soft anchor sheath can be provided with variable density. Soft anchor sheath setting requires deformation of the sheath in a bone tunnel for the sheath to anchor into place. By changing the density of the sheath in certain areas, the sheath deforms in certain areas first, allowing the sheath to anchor in bone in different ways. Variations include the density change in the sheath from a high pick count (H) to a low pick count (L). Versions of the sheath can include HLH or LHL, or HLHL or LHLH, for example, that would allow the sheaths to deform in different ways to anchor in bone. When tension is applied to set the sheath, the bunching or deformation of the sheath occurs differently at/in different areas.

Methods of tissue repairs with variable density soft anchors are also disclosed. An exemplary method includes inter alia the steps of: (i) varying the density of a soft anchor sheath along a length of the sheath; and (ii) employing the sheath for one or more tissue repair applications. The one or more tissue repair applications can include soft tissue repair; orthopedic surgical repairs such as rotator cuff repairs, Achilles tendon repairs, patellar tendon repairs, ACL/PCL reconstructions, hip and shoulder reconstructions, among many others.

Figure 1:
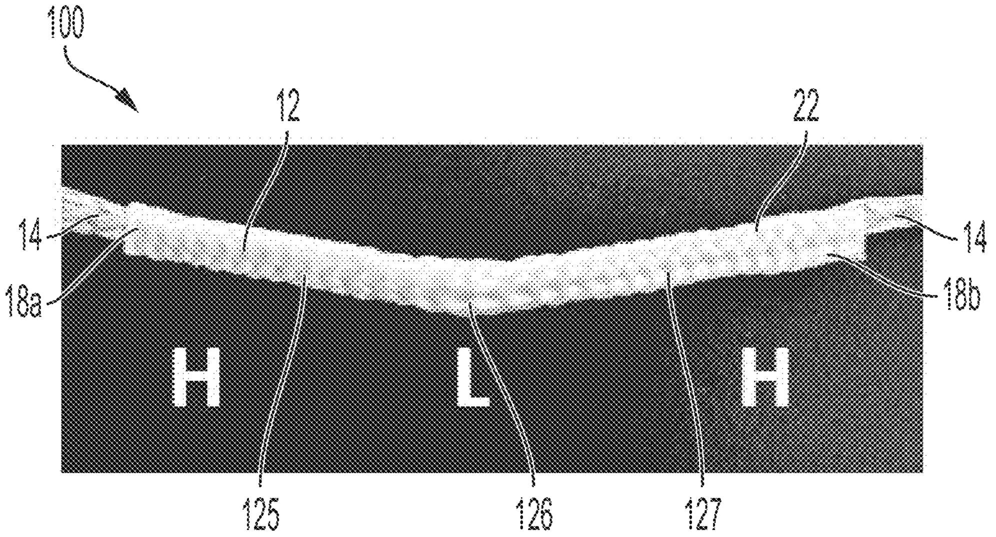
FIG. 1 illustrates a soft anchor sheath.
Figure 2:
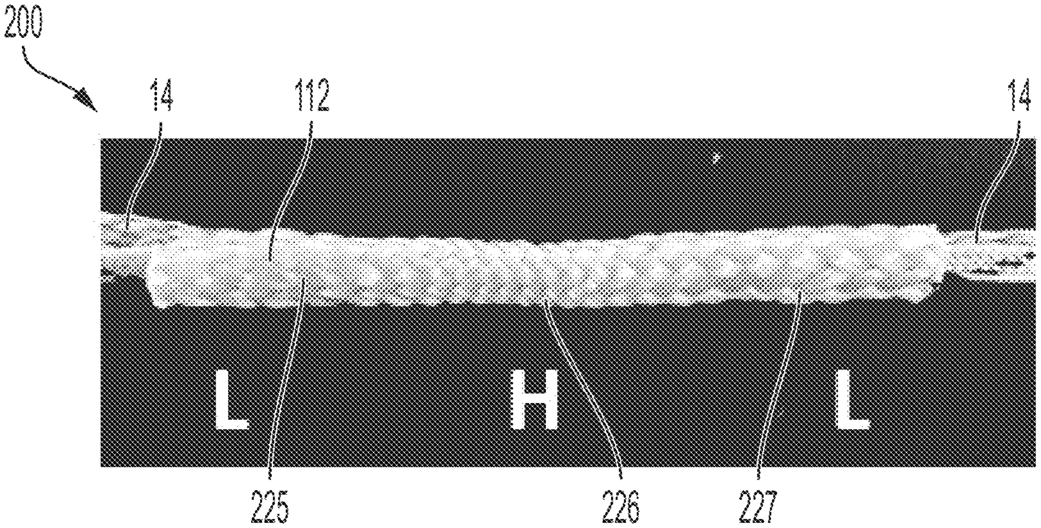
FIG. 2 illustrates another soft anchor sheath.
Figure 7:
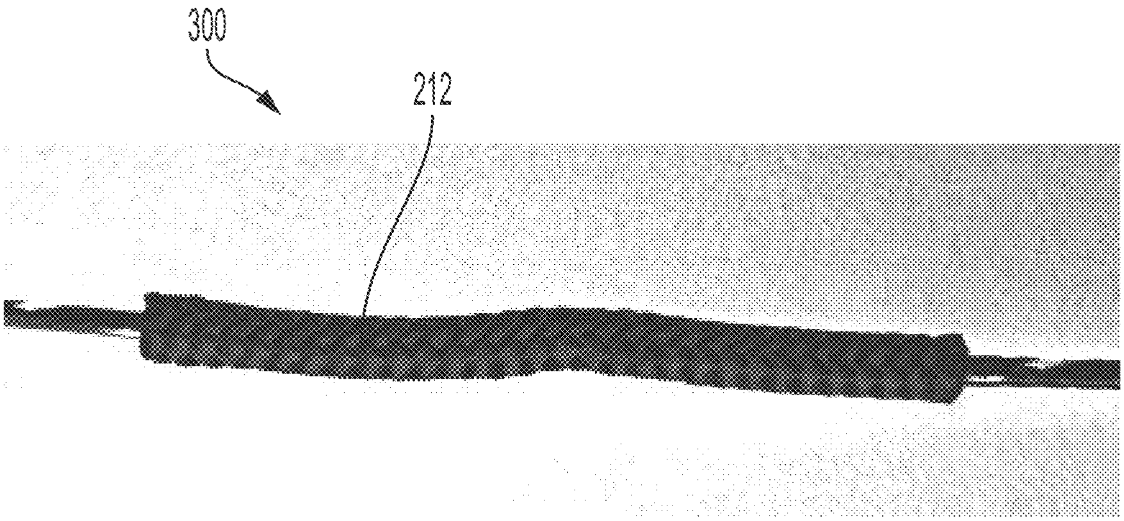
FIG. 7 PRIOR ART
FIG. 7 illustrates a prior art soft anchor sheath.
Figure 8:
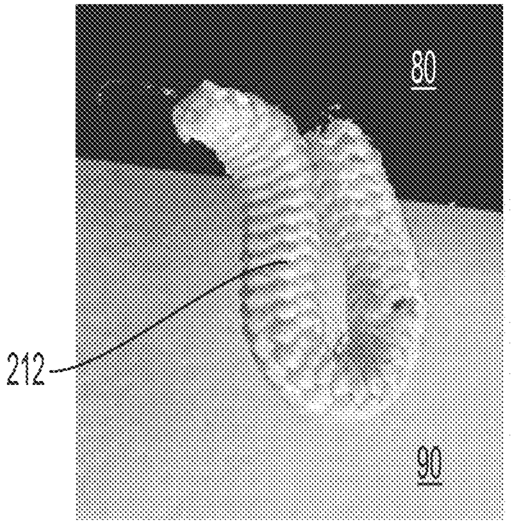
FIG. 8 PRIOR ART
FIGS. 8 and 9 illustrate schematic steps of a tissue repair with the prior art sheath of FIG. 7.
Figure 9:
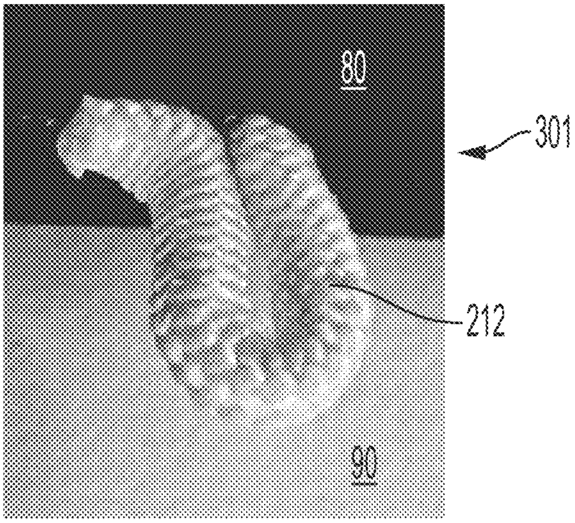
FIG. 9 PRIOR ART

Referring now to the drawings, where like elements are designated by like reference numerals, FIGS. 1 and 2 illustrate exemplary anchor constructs 100, 200 (soft anchors 100, 200; soft anchor sheaths 100, 200; sheaths 100, 200; all-suture anchors 100, 200; surgical constructs 100, 200) of the present disclosure. FIGS. 3-6 illustrate schematic steps of exemplary anchor bunching 101, 201 (tissue repairs 101, 201) with anchor constructs 100, 200. FIG. 7 illustrates a prior art soft anchor construct 300. FIGS. 8 and 9 illustrate schematic steps of prior art tissue repairs 301 with anchor construct 300.

The anchor constructs detailed below are soft anchors formed of "soft" materials, such as suture materials, that confer the ability to be inserted into bone sockets/holes/tunnels and bunch together, collapse, expand and/or change shape to fixate within the socket/hole/tunnel. In some embodiments, the soft anchor includes a sheath and at least one flexible strand attached to the sheath. At least one flexible strand can be fixed (affixed) or slidable relative to the sheath. In other embodiments, the soft anchor includes a sheath and a plurality of flexible strands, wherein some or all of the flexible strands are affixed as non-sliding to the sheath, and wherein some or all of the flexible strands are slideable relative to the sheath. The soft anchors can be utilized in various surgical techniques to attach tissue to bone.

FIG. 1 illustrates a soft anchor 100 including a plurality of regions/sections 125, 126, 127, etc. having different densities (mass densities; M/V) along sheath 12.

Sheath 12 can be in the form of a tubular sleeve or tubular member made of a flexible material, such as a braided, woven, or knitted structure made of yarns, fibers, filaments, sutures or similar materials, or combinations of these materials. In one embodiment, sheath 12 is constructed of ultra-high molecular weight polyethylene (UHMWPE). In one embodiment, sheath 12 is constructed of UHMWPE and polyester. In another embodiment, sheath 12 is constructed of UHMWPE with an elastic component. In another embodiment, sheath 12 is constructed of polyester suture material with an elastic component. The elastic component can be elastane. The elastic component can be incorporated into the sheath via braiding, weaving, and/or knitting. In an embodiment, an elastic sheath can include a combination of elastic, polyester, and UHMWPE all braided in a tubular jacket. In an embodiment, an elastic sheath can consist essentially of elastane, polyester, and UHMWPE. The elastic component provides elasticity while the other components provide strength and limit the elongation of the suture.

In one embodiment, ends of sheath 12 can be brought together. In one embodiment, ends of sheath 12 can be glued. In one embodiment, ends of sheath 12 can be frayed. In one embodiment, sheath 12 can be tape such as suture tape. Sheath 12 can also be any non-tubular structure.

Soft anchor 100 can include at least one flexible strand 14 passing through at least a portion of the sheath 12. Sheath 12 includes a tubular body that extends between opposing ends 18*a*, 18*b*. The opposing ends 18*a*, 18*b* can be open or closed ends. The tubular body establishes a bore that extends between the opposing ends 18*a*, 18*b*. As shown in FIG. 1, one or more flexible strands 14 (flexible coupler 14; suture 14) passes through at least a portion of bore of the sheath 12. Flexible strand 14 can assist in bunching together the sheath 12 once the soft anchor 100 is inserted into bone or secured over bone and the flexible strand 14 is tensioned.

In one embodiment, flexible strand 14 can pass through an opening 22 formed through the tubular body and which is spaced from the opposing ends 18*a*, 18*b* of the sheath 12 (as shown in FIG. 1, for example). The flexible strand 14 can be of any length and can include one or more free ends that extend outside of the sheath 12. This configuration can be used if the opposing ends 18*a*, 18*b* are closed ends. The flexible strand 14 could alternatively pass directly through the opposing ends 18*a*, 18*b* if the opposing ends 18*a*, 18*b* are configured as open ends. Additional strands can be passed through the tubular body of sheath 12, for example, suture passers and/or additional filaments and/or flexible couplers, in same or different orientations, as desired and depending on the specific surgical procedure to be conducted. In additional embodiments, flexible strand 14 can enter and exit the sheath multiple times, at same or different locations. For example, the suture leaving the sheath, enters the sheath and leaves again, to help even further with the bunching.

Flexible strand 14 can be a suture. Non-limiting examples of suitable sutures include FiberWire®, TigerWire®, or FiberChain® suture, although any type of suture may be utilized, including cored or coreless sutures. In another embodiment, flexible strand 14 can be suture tape, such as FiberTape®. Flexible strand 14 can include any soft, flexible strand of material.

Flexible strand 14 can be affixed as non-sliding relative to the sheath 12 (i.e., is not slidable inside the bore to change its positioning relative to the sheath 12) or can slide relative to the sheath 12. Details of flexible strand 14 being affixed as non-sliding relative to sheath 12 can be found, for example, in U.S. Pat. No. 9,622,738 issued on Apr. 18, 2017, assigned to Arthrex, Inc., the disclosure of which is incorporated in its entirety by reference herein.

Soft anchor 100 is configured for use in various soft tissue repairs or fixations and may be fixated inside bone or over bone for attaching tissue (e.g., ligament, tendon, graft, etc.) to bone. For example, the soft anchor 100 can be used in conjunction with a variety of orthopedic surgical repairs, including but not limited to rotator cuff repairs, Achilles tendon repairs, patellar tendon repairs, ACL/PCL reconstructions, hip and shoulder reconstructions, among many others. The fixation can be on or over bone.

Soft anchor 100 is referred to as a "soft" construct because it is formed of soft materials such as yarns, fibers, filaments, strings, fibrils, strands, sutures, etc., or any combination of such materials. The soft materials may be synthetic or natural materials, or combinations of synthetic and natural materials, and may be bio-degradable or non-degradable, and may be elastic or non-elastic within the scope of this disclosure. In one non-limiting embodiment, the soft anchor 100 is made exclusively of soft, suture-based materials.

As detailed below, the soft anchor 100 can be manufactured via braiding weaving and/or knitting processes, or combination of these processes, with or without an elastic component in them, and with a variable pick count throughout that allows the soft anchor 100 to deform according to the pick count.

As shown in FIG. 1, sheath 12 of soft anchor 100 includes a plurality of segments/portions/regions/lengths having different densities. In a non-limiting embodiment, sheath 12 includes a first portion 125 (first segment 125; first length 125; first region 125) adjacent a second portion 126 (second segment 126; second length 126; second region 126) which in turn is adjacent a third portion 127 (third segment 127; third length 127; third region 127). In one embodiment, one of the first, second, and third portions 125, 126, 127 can have a first density (first mass density; first braid pattern density; first pick per inch; first programable pick per inch (PPI)), wherein the adjacent portions have a second density (second mass density; second braid pattern density; second pick per inch; second programable pick per inch (PPI)). The first density is different from the second density.

One of the first, second, and third portions 125, 126, 127 can be a high-density (H) portion, wherein the other remaining portions are low-density (L) portions. In other embodiments, one of the first, second, and third portions 125, 126, 127 can be a low-density (L) portion, wherein the other remaining portions are high-density (H) portions. In an exemplary embodiment, L can be of about 2 mm and H can be of about 3 mm.

In one embodiment, portions or segments of sheath 12 can alternate in a pattern of high- and low-density segments along a length of the sheath. In one embodiment, high- and/or low-density segments or portions of sheath 12 can alternate in a random manner along the length of the sheath. In yet additional embodiments, regular patterns of high- and/or low-density segments can alternate with randomly provided segments (high- and/or low-density segments) along the length of the sheath. In additional embodiments, different segments of the sheath can be provided with two or more different densities, wherein the two or more densities are all different. The different segments of the sheath can have different lengths and/or different diameters and/or compositions.

FIG. 1 illustrates an exemplary embodiment of sheath 12 of soft anchor 100 with first and third segments 125, 127 provided as H density segments and the second segment 126 as L density segment. In an exemplary-only embodiment, L can be of about 2 mm and H can be of about 3 mm.

FIG. 2 illustrates an exemplary embodiment of sheath 212 of soft anchor 200 with first and third segments 225, 227 provided as L density segments and the second segment 226 as H density segment.

Although the embodiments of FIGS. 1 and 2 have been described with reference to only three segments or regions of sheath 12, 112 of different densities, it must be understood that the disclosure is not limited to these exemplary-only embodiments. Accordingly, the disclosure contemplates any number of segments, regions, lengths, portions of the tubular sheath, provided with at least two different densities, and in a regular or non-regular pattern. The number and length of sections can vary along the length of the sheath 12, 112 in a regular or non-regular pattern. The number of densities can also vary. Sheath 12, 112 can be provided with any number of segments having any number of varying densities, all different. The length of the segments can be also different, according to the specific anchor bunching repair.

Soft anchors 100, 200 can be woven suture structures constructed with a parallel, twisted and/or braided, knitted, woven monofilament in the warp or weft direction. Density behavior can be manipulated via the amount or composition of fibers braided together (for example, by the addition of a monofilament), to create different-density segments along the sheath length. One or more filaments of elastic material such as elastane can be incorporated into the sheath.

Soft anchors 100, 200 can be constructed in such a way that the monofilament and/or elastic material can be diverted, inserted, or removed at desired locations regardless of the suture configuration which creates high- and low-density segments within the same suture braid/sheath. Soft anchors 100, 200 can be fabricated as a one-piece construct.

Tubular sheath 12, 112 of round and/or oval cross-sections can be manufactured via braiding, weaving and/or knitting processes with a monofilament and/or elastic component incorporated in the remaining carriers (bundles). In an exemplary-only embodiment, sheath 12, 112 can include a single monofilament incorporated within 15 carriers to form one or more H density segments as part of a sheath. Sheath 12, 112 can also include an elastic component.

Figure 3:
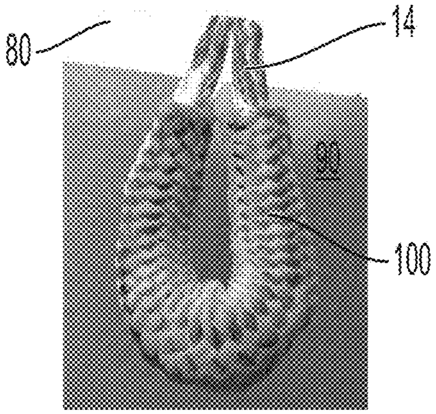
FIGS. 3 and 4 illustrate schematic steps of a tissue repair with the anchor sheath of FIG. 1.
Figure 4:
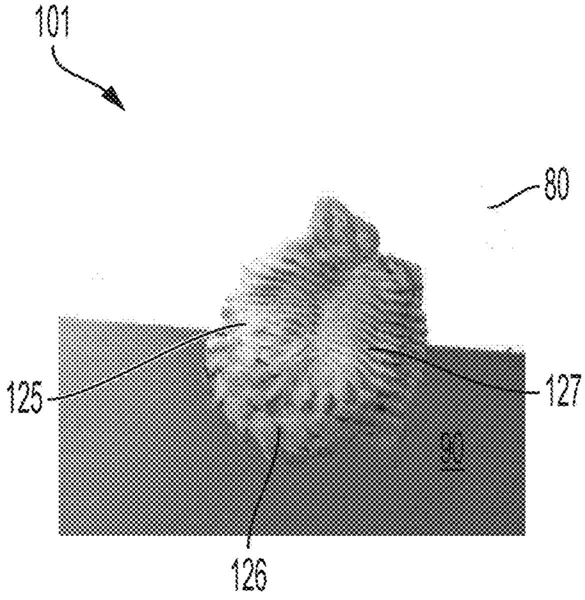

FIGS. 3 and 4 schematically illustrate soft anchor 100 securing first tissue 80 to second tissue 90 as part of anchor bunching 101 (surgical repair 101). FIGS. 3 and 4 illustrate soft anchor 100 inserted past first tissue 80 (for example, cortical bone) to second tissue 90 (for example, cancellous bone) as part of repair 101. Sheath 12 is secured against first tissue 80 (bone 80) so that the density change in the sheath material allows increased bunching and deformation within the bone hole, socket, or tunnel, allowing the sheath to anchor in different ways and to increase the overall fixation. Flexible coupler 14 can be passed through tissue to secure it to bone.

Figure 5:
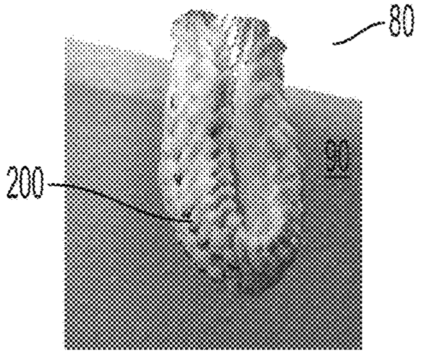
FIGS. 5 and 6 illustrate schematic steps of a tissue repair with the anchor sheath of FIG. 2.
Figure 6:
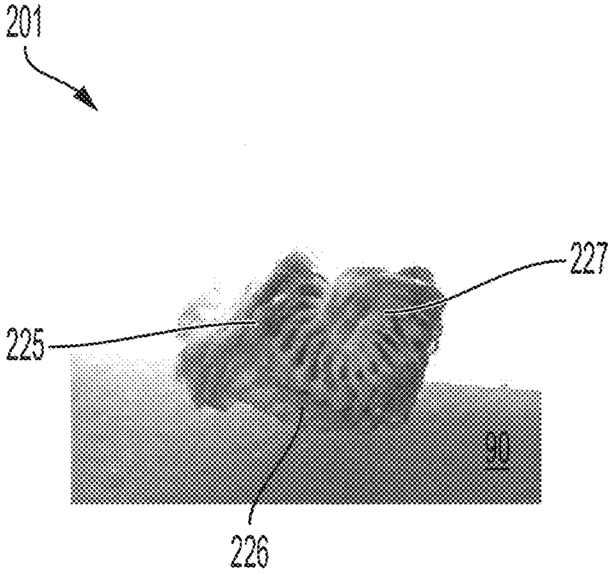

Similarly, FIGS. 5 and 6 schematically illustrate soft anchor 200 securing first tissue 80 (for example, soft tissue) to second tissue 90 (for example, bone) as part of anchor bunching 201 (surgical repair 201). Sheath 112 is secured into second tissue 90 (bone 90) so that the density change in the sheath material allows increased bunching and deformation within the bone hole, socket, or tunnel, allowing the sheath to anchor in different ways and to increase the overall fixation. Flexible coupler 14 can be passed through tissue to secure it to bone.

Flexible coupler 14 of repairs 101, 201 can be employed for attachment of soft tissue 80 to bone 90 by passing the flexible coupler through or around soft tissue and forming at least one adjustable, flexible, continuous, knotless, tensionable loop around or through soft tissue 80. One or more flexible couplers 14 and optional shuttling strands may extend through the bore of sleeve 12, 112 in similar or different directions and/or orientations and/or locations. The flexible tubular sleeve 12, 112 with the flexible couplers and shuttling strands may be secured into or onto bone, and flexible strands can pass over soft tissue (rotator cuff) and are secured into bone to approximate soft tissue to bone. Details of an exemplary soft suture anchor with a soft anchor sleeve (sheath or tubular member) and flexible shuttling strands are set forth, for example, in U.S. Pat. No. 10,849,734 issued Dec. 1, 2020, entitled "Methods of Tissue Repairs," the disclosure of which is incorporated by reference in its entirety herein.

Flexible coupler 14 can be further attached to one or more fixation devices such as any anchors, for example, knotted anchors, knotless anchors, or all-suture anchors, or any devices that confer secure attachment and fixation of soft tissue 80 over bone 90. The fixation device can be a knotless anchor such as a two-piece Arthrex PushLock® anchor, disclosed in U.S. Pat. No. 7,329,272, or an Arthrex SwiveLock® anchor, disclosed in U.S. Pat. Nos. 8,012,174 and 9,005,246, the disclosures of both of which are fully incorporated by reference in their entirety herein. The fixation device can also be another all-suture soft anchor like soft anchors 100, 200 detailed above. Flexible coupler 14 can consist essentially of elastic suture.

Another exemplary fixation device is a soft anchor or an "all-suture" anchor. A soft anchor (soft suture anchor or all-suture soft knotless anchor) is provided with a soft anchor sleeve (sheath or tubular member) with two open ends, and at least two flexible shuttling strands extending through the soft anchor sleeve (sheath).

FIGS. 7-9 illustrate a prior art soft anchor 300 securing first tissue 80 (for example, soft tissue) to second tissue 90 (for example, bone) as part of prior art surgical repair 301. Sheath 212 secured into second tissue 90 (bone 90) has no density change in the sheath material and, thus, the bunching and deformation is minimal relative to repairs 101, 201 detailed above.

Methods of manufacturing soft anchor sheaths with varied densities and/or elasticities are also disclosed. An exemplary method of making a soft anchor sheath 12, 112 includes the step of incorporating a monofilament and optionally an elastic component into the sheath via braiding, weaving, and/or knitting, to form a regular or non-regular braid density pattern into the sheath 12, 112. The method can further include the step of attaching one or more flexible strands 14 to the soft anchor sheath 12, 112. The one or more flexible strands 14 can be elastic.

A method of soft tissue reconstruction comprises attaching soft tissue 80 to bone 90 with at least one soft anchor 100, 200. The method can include forming at least two different densities sections along a length of sheath 12, 112 of soft anchor 100, 200; attaching at least one flexible coupler 14 to the sheath 12, 112; and securing the soft anchor 100, 200 into bone. The method can also include securing the soft anchor 100, 200 into bone 90 so that the at least two different densities sections bunch in different ways within bone 90; and passing the at least one flexible coupler 14 through or around soft tissue 80 to attach the soft tissue to bone. The method can further include forming, with the at least one flexible coupler 14, at least one adjustable, flexible, continuous, knotless, tensionable loop around or through soft tissue 80. The method can further include securing the at least one flexible coupler 14 to a fixation device. The fixation device can be a knotless anchor. The fixation device can be a hard body anchor. The fixation device can be a soft anchor. The at least one flexible coupler 14 can consist essentially of elastic suture. The soft tissue 80 can be rotator cuff. A plurality of soft anchors 100, 200 can be used for a soft tissue repair, such as a rotator cuff repair.

The constructs and methods of the present disclosure provide increased fixation and consistent longer lasting longer pressure on the tissue.

The constructs of the present disclosure have applicability to any tissue repair and surgical procedure such as, for example, rotator cuff repairs, Achilles tendon repair, patellar tendon repair, ACL/PCL reconstruction, hip and shoulder reconstruction procedures, and applications for elastic suture used in or with suture anchors. The surgical constructs and repair methods of the present disclosure can be employed in tissue repairs that do not involve knot tying, for example, for use with suture anchors (such as PushLock® and/or SwiveLock® suture anchors) or for knotless arthroscopic suture repairs (such as knotless single row rotator cuff repair, or SpeedBridge™ repairs using no knots and only suture passing steps), among many others.

An exemplary SutureBridge™ tendon repair technique, developed by Arthrex, Inc., and disclosed in U.S. Pat. No. 8,012,174 (the disclosure of which is herein incorporated by reference in its entirety) consists of a tied medial row constructed with two threaded suture anchors, combined with knotless lateral fixation using two Arthrex PushLocks® constructs. The construct enhances footprint compression and promotes tendon healing-to-bone with minimal knot tying.

An exemplary SpeedBridge™ technique, also developed by Arthrex, Inc., and disclosed in U.S. Pat. No. 9,005,246 (the entire disclosure of which is herein incorporated by reference) uses a threaded swivel anchor which can be combined with any of constructs 100, 200 to create a quick and secure SutureBridge™ construct with no knots and only two suture passing steps.

A method of soft tissue reconstruction comprises attaching soft tissue 80 to bone 90 with at least one surgical construct 100, 200. The method can further comprise securing the surgical construct 100, 200 to bone 90; and securing at least one flexible coupler 14 to soft tissue 80. The surgical construct 100, 200 can be a one-piece construct comprising elastic material. The flexible coupler 14 can comprise elastic material. The method can further comprise attaching flexible coupler 14 to a fixation device. The fixation device can be a knotless or knotted anchor.

Flexible coupler 14 can be formed of a high strength suture material such as FiberWire® suture, sold by Arthrex, Inc. of Naples, Fla., and described in U.S. Pat. No. 6,716,234, the disclosure of which is incorporated by reference herein. FiberWire® suture is formed of an advanced, high-strength fiber material, namely ultrahigh molecular weight polyethylene (UHMWPE), sold under the tradenames Spectra® (Honeywell International Inc., Colonial Heights, Va.) and Dyneema® (DSM N.V., Heerlen, the Netherlands), braided optionally with at least one other elastic fiber, natural or synthetic, to form lengths of suture material. Flexible coupler 14 can also include suture tape such as FiberTape® suture tape (as disclosed in U.S. Pat. No. 7,892,256, the disclosure of which is incorporated in its entirety herewith) or collagen tape, or wide "tape like" material, or combinations thereof.

Flexible coupler 14 can consist essentially of suture material and elastane, or combination of suture material and elastane and other materials such as long chain synthetic polymers like polyester and nylon, or materials such as PET, silk nylon or absorbable polymers, or coating materials (such as wax, silk, or silicone products), among many others. Flexible coupler 14 can consist of strands with cross-sections of various forms and geometries, including round, oval, rectangular, or flat, among others, or combinations of such forms and geometries. In an embodiment, at least one flexible coupler 14 can be provided as a suture which is braided, knitted or woven.

Parts or all of soft anchor 100, 200 including sheath 12, 112 and flexible coupler 14 can be also coated and/or provided in different colors. In an embodiment, parts (or all) of sheath 12, 112 and flexible coupler 14 can be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the construct, pliability, handleability or abrasion resistance, for example.

Parts or all of sheath 12, 112 and/or flexible coupler 14 can be also provided with tinted tracing strands, or otherwise contrast visually with other parts of the construct, which remain a plain, solid color, or displays a different tracing pattern, for example. Various structural elements of the surgical constructs may be visually coded, making identification and handling of the suture legs simpler. Easy identification of suture in situ is advantageous in surgical procedures.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

What is claimed is:

1. A soft anchor comprising:

a tubular sheath having a body with a first end and a second end opposite the first end and a middle located between the first end and the second end, wherein the middle has a mass density different from mass densities of the first end and the second end; and at least one flexible coupler passing at least once through the tubular sheath.

2. The soft anchor of claim 1, wherein the tubular sheath has at least one segment of a first mass density and at least another segment of a second mass density, wherein the first mass density is greater than the second mass density.

3. The soft anchor of claim 2, wherein the tubular sheath has two segments of the first mass density and one segment of the second mass density.

4. The soft anchor of claim 2, further comprising a first plurality of segments of the first mass density and a second plurality of segments of the second mass density, wherein the first plurality of segments and the second plurality of segments form a pattern along a length of the tubular sheath.

5. The soft anchor of claim 1, wherein the tubular sheath includes a monofilament braided, weaved, or knitted with additional filaments.

6. The soft anchor of claim 1, wherein the at least one flexible coupler enters the tubular sheath at a first location, extends within the tubular sheath, and exits the tubular sheath at a second location, wherein the second location is different from the first location.

7. The soft anchor of claim 6, wherein the first location is a first open end of the tubular sheath, and wherein the second location is a second open end of the tubular sheath.

8. The soft anchor of claim 1, wherein the soft anchor is an all-suture anchor, and the flexible coupler is round suture.

9. The soft anchor of claim 1, wherein the tubular sheath consists essentially of polyester and UHMWPE.

10. The soft anchor of claim 1, wherein the tubular sheath consists essentially of polyester, UHMWPE and elastane.

11. The soft anchor of claim 1, wherein the tubular sheath is elastic.

12. The soft anchor of claim 1, wherein the tubular sheath is non-elastic.

13. The soft anchor of claim 1, wherein the soft anchor is manufactured as a one-piece construct.

14. The soft anchor of claim 1, wherein the mass density of the middle is smaller than the densities of the first end and the second end.

* * * * *